United States Patent [19]
Hill et al.

[11] Patent Number: 5,850,804
[45] Date of Patent: Dec. 22, 1998

[54] MILK COMPOSITIONS HAVING LOW FOULING RATES SELECTED BY REFERENCE TO β-LACTOGLOBULIN PHENOTYPES

[75] Inventors: Jeremy Paul Hill; Michael John Boland; Andrew Faulks Smith, all of Palmerston North, New Zealand

[73] Assignee: New Zealand Dairy Board, Wellington, New Zealand

[21] Appl. No.: 776,202

[22] PCT Filed: May 22, 1996

[86] PCT No.: PCT/NZ96/00045

§ 371 Date: Jun. 9, 1997

§ 102(e) Date: Jun. 9, 1997

[87] PCT Pub. No.: WO96/36240

PCT Pub. Date: Nov. 21, 1996

[30] Foreign Application Priority Data

May 19, 1995 [NZ] New Zealand ............................ 272161

[51] Int. Cl.$^6$ ...................................................... A01J 5/007
[52] U.S. Cl. .......................................................... 119/14.02
[58] Field of Search .............................. 119/14.01, 14.02, 119/14.03, 14.08, 14.14

[56] References Cited

FOREIGN PATENT DOCUMENTS

88236/91 (651148)  6/1992  Australia .

OTHER PUBLICATIONS

Hill, J P (1993) "The relationship between β–lactoglobulin phenotypes and milk composition in New Zealand dairy cattle", Journal of Dairy Science, 76, 281–286.

Hill, JP, Boland, MJ & Creamer, LK (1993) "The alteration of bulk milk composition thorugh the selection of β–lactoglobulin phenotypes", Livestock Production Science, 35, 192–193.

Hill, JP & Paterson, GR (1994) "The variation in milk composition from individual β–lactoglobulin AA and BB phenotype cows", Proceedings of the New Zealand Society of Animal Production 54, 293–295.

Hill, JP, Paterson, GR, Lowe, R & Wakelin, M (1995) "The effect of season and β–lactoglobulin phenotype on milk composition", Proceedings of the New Zealand Society of Animal Production 55, 94–96.

Medrano, JF & Aguilar–Cordova, E (1990) "Polymerase chain reaction amplification of bovine β–lactoglobulin genomic sequences . . . ", Animal Biotechnology, 1, 73–77.

Newstead, DF & Baucke, AG (1983) "Heat stability of recombined evaporated milk and reconstituted concentrated skim milk: Effects of temperature . . . ", New Zealand Journal of Dairy Science & Tech., 18, 1–11.

Ng–Kwai–Hang, KF and Grosclaude, F (1992) "Advanced Dairy Chemistry" vol. 1: Proteins (Ed. Fox PF) Elsevier Science Publishers Ltd., London, pp. 405–445.

(List continued on next page.)

*Primary Examiner*—Thomas Price
*Attorney, Agent, or Firm*—Knobbe, Martens, Olson & Bear, LLP

[57] ABSTRACT

This invention is based on the discovery that there is a relationship between the fouling rate of milk during processing into milk powder products and the β-lactoglobulin phenotype of the cow whose milk is being processed. Milk from β-lactoglobulin BB phenotype cows has a much lower fouling rate than that from β-lactoglobulin AA phenotype cows. The invention consists in a method comprising testing milk from identified cows for the presence of non-fouling β-lactoglobulin variants and recovering and maintaining that milk separate from the fouling variant containing milk. The non-fouling variant or blends of at least 30% by weight of the non-fouling variant are further processed into milk powder products. The invention also consists in a method of selecting a diary herd having only β-lactoglobulin non-fouling variant phenotype cows.

23 Claims, 8 Drawing Sheets

OTHER PUBLICATIONS

Paterson, GR, Hill, JP & Otter, DE (1995) "Separation of β–lactoglobulin A, B and C variants of bovine whey using capillary zone electrophoresis", Journal of Chromatography A, 700, 105–110.

Singh, H & Creamer, LK (1991) "Denaturation, aggregation and heat stability of milk protein during the manufacture of milk powder", Journal of Diary Research, 58, 269.

Milchwissenschaft, vol. 49, No. 3 (1994), G Lopez–Galvez et al. "Genetic polymorphism of whey proteins in two ovine breeds", pp. 123–125.

Milchwissenschaft, vol. 50, No. 12 (1995), R Lowe et al. "Simultaneous separation of the β–lactoglobulin A, B and C variants using polyacrylamide gel electrophoresis", pp. 663–666.

Journal of Dairy Science, vol. 78 (suppl. 1) (1995), G Bode et al. "Effect of β–lactoglobulin phenotype on milk composition of Holstein cattle".

Journal of Diary Research, vol. 51, No. 4 (1984), DM McLean et al. "Effects of milk protein genetic variants on milk yield and composition", pp. 531–546.

5,850,804

MILK COMPOSITIONS HAVING LOW FOULING RATES SELECTED BY REFERENCE TO β-LACTOGLOBULIN PHENOTYPES

TECHNICAL

This invention relates to a method for the manufacture of skim milk powders and whole milk powders with improved properties. More particularly, the method relates to the selection of milk from cows producing milk which contains only the B variant of β-lactoglobulin.

BACKGROUND ART

Plant Fouling

The deposition of milk constituents on milk processing plant surfaces (fouling), particularly on heat exchanger surfaces, is an undesirable consequence of milk processing. Fouling can reduce the rate of heat transfer into the milk and increase the pressure drop across the heating equipment used. In addition, foulant material can act as a medium for the growth of bacteria, potentially compromising milk product sterility and safety. At some point during the heat processing of milk the level of fouling reaches a point at which processing must be interrupted to allow for plant cleaning. Cleaning of plant involves the use of expensive chemicals and this in combination with the reduced process run times, means that high rates of fouling can have a significant economic impact for the milk processor.

Milk Composition

It is known that there is a relationship between β-lactoglobulin phenotypes and milk compositions in dairy cattle. Bulk milk collected from β-lactoglobulin AA phenotype cows had a composition which was markedly different from that of β-lactoglobulin BB phenotype cows (Hill, 1993). The β-lactoglobulin AA phenotype bulk milk had 28% higher whey protein concentrations, 7% lower casein protein concentrations, 11% lower fat concentrations and 6% lower solids concentrations than β-lactoglobulin BB phenotype bulk milk. The higher whey protein concentrations in β-lactoglobulin AA phenotype bulk milk resulted from large increases in β-lactoglobulin concentrations in this type of milk. However, concentrations of α-lactoglobulin were lower in β-lactoglobulin AA phenotype bulk milk. It is believed that the high concentrations of β-lactoglobulin or the presence of β-lactoglobulin A variant gene suppresses the synthesis of other milk proteins (Hill, 1993).

It has not previously been reported that differing milk compositions due to β-lactoglobulin phenotypes give rise to different fouling rates. It would be desirable to be able to choose compositions with the lowest fouling rate and to select dairy cattle phenotypes to produce such compositions.

It is an object of this invention to go some way towards achieving this desideratum or at least to offer the public a useful choice.

DISCLOSURE OF THE INVENTION

Accordingly, the invention may be said broadly to consist in a method of selecting milk for milk powder manufacturing properties which comprises testing milk from identified cows for the presence of variants of β-lactoglobulin and selecting those cows whose milk contains any non-fouling variant and does not contain any fouling variant, and milking separately the non-fouling variant milk producing cows and recovering and maintaining their milk separately from milk from any other source.

Preferably said non-fouling variant is the B variant of β-lactoglobulin.

Preferably said fouling variant is the A variant of β-lactoglobulin.

Preferably said resultant milk is tested for the presence of any fouling variant and discarded if any is found.

Preferably said process includes the additional step of processing said milk into a milk powder product.

Preferably said additional step comprises UHT processing.

Preferably said method of testing is a phenotyping method.

In one alternative said phenotyping method is capillary electrophoresis.

In another alternative said phenotyping method comprises polyacrylamide gel electrophoresis.

The invention may be said broadly to consist in milk selected according to any one of the processes herein above defined.

The invention may also be said broadly to consist in a milk powder product prepared by any one of the processes described herein above.

In another embodiment the invention may be said broadly to consist in a method for selecting breeding cows which produce daughters whose milk is non-fouling which comprises determining the genotype of said cows and selecting those whose daughters produce milk which does not contain the A variant of β-lactoglobulin.

Alternatively, the invention may be said broadly to consist in a process for selectively breeding bulls which produce daughters whose milk does not contain the A variant of β-lactoglobulin which comprises determining the genotype of said bulls and selecting those which daughters which produce milk which does not contain the A variant of β-lactoglobulin.

Preferably, the phenotyping of daughters to determine the genotype of said bull is done by testing the milk of said daughters for absence of fouling variants of β-lactoglobulin and the presence of non-fouling variants of β-lactoglobulin.

Alternatively, said cows or bulls are genotyped directly by using appropriate probes and polymerase chain reaction technology.

In another embodiment the invention may be said broadly to consist in cows selected in accordance with the immediately preceding method.

In a still further embodiment the invention may be said broadly to consist in bulls selected in accordance with the above defined method.

In a still further embodiment the invention may be said broadly to consist in semen of bulls selected in accordance with the above defined method.

In an alternative to any of the above processes or products the milk or milk product is goat's milk or milk product, sheep's milk or milk product, buffalo's milk or milk product, or milk or milk product from any other mammal which is fit for human consumption.

In a further embodiment the invention consists in a method of selecting milk as defined above including the additional step of blending up to 70% by weight of the combination of fouling milk with no less than about 30% by weight of the non-fouling milk.

The invention also consists in a blend of up to 70% by weight of the combination of fouling milk with no less than 30% by weight of the non-fouling milk.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

BRIEF DESCRIPTION OF THE DRAWINGS

The invention may be more fully understood by having reference to the accompanying drawings wherein.

MODES OF CARRYING OUT THE INVENTION

Milk Protein Genetic Variants

Figure 1:
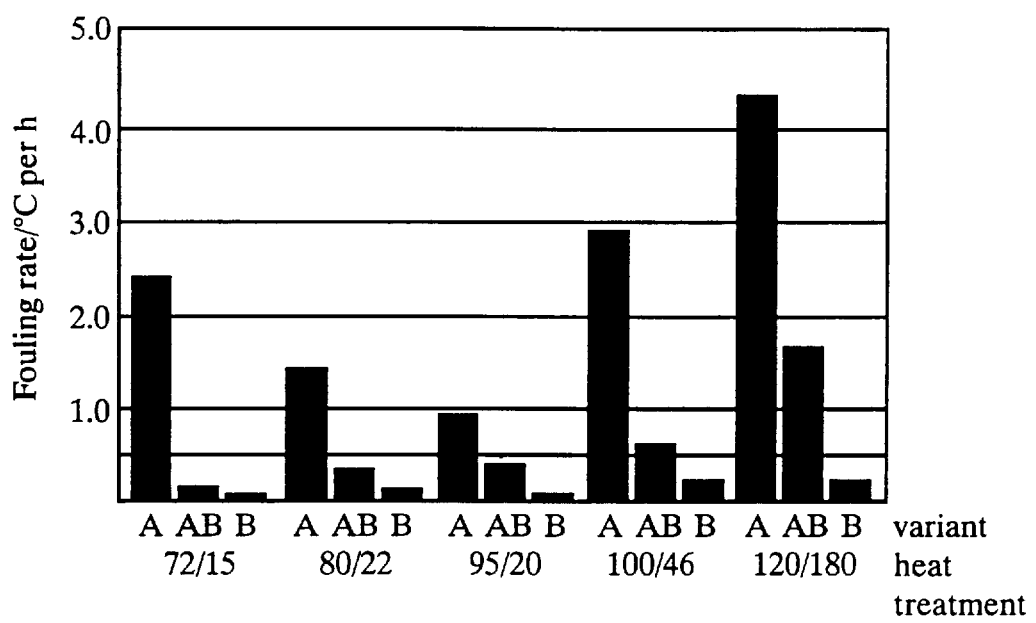
FIG. 1 is a bar graph comparing the UHT fouling rates of the genetic variants and controls in Trial 1, an early season or spring trial (Example 2). In the bottom line the figure before the slash is the temperature and the figure after the slash is the treatment time in seconds.
Figure 2:
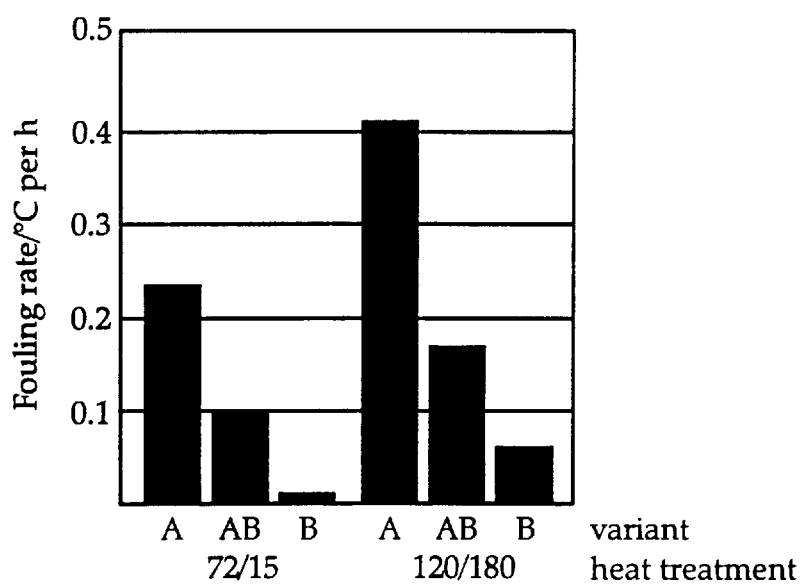
FIG. 2 is a bar graph setting out the same parameters in respect of Trial 2, an autumn trial.
Figure 3:
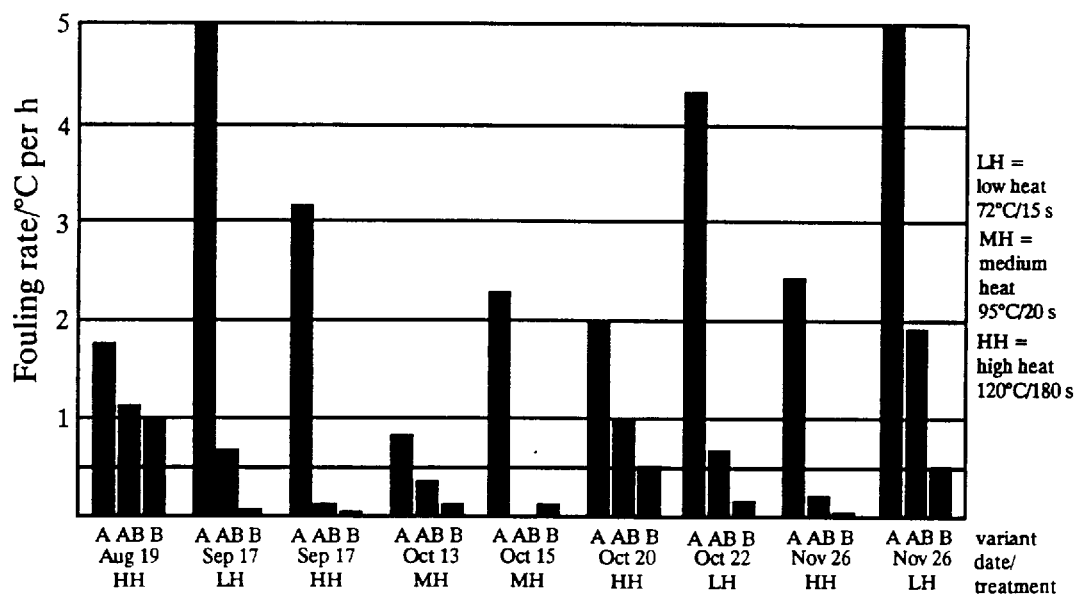
FIG. 3 is a similar bar graph in respect of whole milk powders in Trial 3, an early to mid spring trial.

Most of the major milk proteins exist in a number of variant forms (Ng-Kwai-Hang and Grosclaude, 1992). The major whey protein in milk, β-lactoglobulin (β-LG) is found in two common forms (the A and B variants). Cows can produce only one variant of β-LG in milk (AA or BB phenotype cows) or a mixture of A and B variants of β-LG in milk (AB phenotype cows). The milk supplied to dairy factories is composed of a mixture of all three phenotype milks. The relative frequencies of β-LG phenotypes in the New Zealand cow population is shown in Table 1.

TABLE 1

Relative frequency of β-LG Phenotypes in New Zealand Cows*.

| AA | AB | BB |
|----|----|----|
| 19 | 50 | 31 |

*10261 cows were phenotyped for β-LG A and B variants.

EXAMPLE 1

Milk Protein Phenotyping

Milk samples from individual cows were phenotyped for β-LG A and B variants using polyacrylamide gel electrophoresis (PAGE) run under non reducing conditions as described by Singh and Creamer (1991).

Capillary Electrophoresis β-LG C Phenotyping Method

Whey was made from the milk samples supplied from individual cows by removal of casein by acid precipitation at pH 4.6 using hydrochloric acid. These whey samples were then subjected to free zone capillary electrophoresis (uncoated capillary—72 cm total length, 50 cm effective length and 50 μm internal diameter) on an Applied Biosystems 270-HT CE system (Foster City, Calif., USA). Samples were injected at the anode using vacuum (17 kPa) for 4 seconds. The individual proteins in the whey samples were separated using a 2-(N-morpholino) ethane sulphonic acid buffer at pH 8.0 and a voltage of 20 kV followed by detection by absorbance at 215 nm. The whey proteins were eluted from the capillary in the order α-lactalbumin, β-LG C variant, β-LG B variant, β-LG A variant, bovine serum albumin. In this way the milk samples from individual cows were phenotyped for β-LG variants. The C variant is less common than the β-LG A and B variants and is only present at low frequencies in the milks from the Jersey cattle breed.

Other Methods

Other methods which may be used for β-LG phenotype identification are summarized by Ng-Kwai-Hang and Grosclaude (1992) and include a variety of alternate electrophoresis techniques: paper electrophoresis, reduced and non reduced PAGE and starch gel electrophoresis, agar gel electrophoresis and a variety of isoelectric focusing techniques. Other phenotyping methods include HPLC on reverse phase or anion exchange columns.

Alternatively it is possible to identify the β-LG genotype of bull sires using the polymerase chain reaction and restriction fragment length polymorphism (Medrano and Aguilar-Cordova, 1990).

EXAMPLE 2

Milk Segregation, Collection and Processing

Trials 1 and 2

The selection and segregation of the milks used in Trials 1 and 2 is described by Hill (1993). Milk was collected from 41 β-LG AA phenotype Friesian cows and 56 β-LG BB phenotype Friesian cows. These milks together with a control of bulk milk from a local dairy factory were processed into a range of whole milk powders in a spring trial (Trial 1) and an autumn trial (Trial 2) in a pilot-plant facility. The recombined milk powders were then subjected to a number of functional tests of UHT fouling properties as described below

Trial 3

To confirm the findings of Trials 1 and 2, Trial 3 was performed in early to mid spring. Milk for this trial was collected from approximately 200 β-LG AA phenotype cows and 200 β-LG BB phenotype cows (Friesian, Jersey and cross-breeds). The selection, segregation and collection of these milks is described by Hill and Paterson (1994).

EXAMPLE 3

Effect of β-LG Variant on Milk Powder Manufacture

To examine the effect of β-LG variant on the manufacture of milk powder, a further trial was performed using the milk supply described in Trial 3. This trial was primarily designed to examine the effect of β-LG variant on the fouling of a milk powder manufacturing plant. The three milk types were pasteurized at 73° C. for 15 seconds, cooled to less than 18° C. and stored in refrigerated silos at 4° C. Milk was pumped to an evaporator feed balance tank to maintain the balance tank level between 10–20 kg. The milk was pumped out of the balance tank at 100 kg/h and heated in a plate heat exchanger (PHE) from 15–20° C. to 85° C. The heated milk was then cooled (in a second PHE) and collected in a refrigerated vat prior to disposal.

The PHE was heated using hot water at a flow rate of approximately 200 kg/h. The hot water temperature was controlled by varying the flow of steam to a steam/cold water mixer (DSI unit). The hot water set point was set automatically based on the desired outlet milk temperature and a five minute average of the difference between the hot water temperature and the outlet milk temperature (approach temperature). The inlet milk temperature and outlet water temperatures were also monitored.

The PHE used for heating was a Pasilac-Therm Type T4RV from Pasilac Therm A/S, Kolding, Denmark. It is designed to heat 400 l milk/h from 4° C. to 70° C. using 800 l/h water supplied at 71° C. It has 30 plates and seven passes. Milk was passed through the PHE until the approach temperature reached 15° C. The PHE was stripped and the plates cleaned and reassembled before CIP treatment with caustic and acid between each run.

EXAMPLE 4

Manufacture of Milk Powders Used for UHT

Prior to processing the β-LG AA, β-LG BB and control milk (β-LG AB type milk) were stored separately at 4° C. in refrigerated vats. Each milk type was separated, pasteurized and standardized prior to processing. All milk types were subjected to a range of preheat treatments from low heat (72° C./15s) to high heat (120° C./180s) prior to evaporation and spray-drying. On entering the evaporator the milk was first heated to 72° C. in heat recovery coils before passing through a direct steam injection (DSI) unit to raise it to the required preheat temperature. The conditions used are set out in Table 2.

TABLE 2

| °C. | Seconds |
|---|---|
| Trial 1 Preheat Treatments (WMP) | |
| 72 | 15 |
| 80 | 22 |
| 95 | 20 |
| 100 | 46 |
| 120 | 180 |
| Trial 2 Preheat Treatments (WMP) | |
| 72 | 15 |
| 20 | 180 |
| Trial 3 Preheat Treatments (WMP) | |
| 72 | 15 |
| 95 | 20 |
| 120 | 180 |
| Trial 3 Preheat Treatments (SMP) | |
| 120 | 180 |

From the DSI unit the milk flowed through holding tubes of known volume, to give the required holding time and was then cooled to 70° C. in a flash vessel and fed into a pilot scale (evaporative capacity 1800 kg h$^{-1}$) triple effect falling-film evaporator (Wiegand GmbH, Karlsruhe, Germany). The concentrate was fed to a pilot scale (125 kg h$^{-1}$) De Laval tall-form spray drier (De Laval Separator Company, Spray Division, River Falls, Wis., USA) via a balance tank.

In between batches or when the preheat tubes were being changed, the spray drier used concentrate from the balance tank and the evaporator was run on water. For Trials 1 and 3, the WMP made using a preheat treatment of 95° C./22s was agglomerated by returning the fines to the spray drier nozzle. For each preheat temperature-time combination and for each milk type, a 50 kg powder sample was collected. The powder produced whilst the evaporator and preheat conditions were reaching steady state was discarded.

EXAMPLE 5

UHT Processing

The WMPs were reconstituted to 12.65% total solids (w/w) and the SMP recombined to 12.65% total solids (w/w). The reconstituted and recombined milks were then stored at 4° C. with agitation, for 1–2 h prior to UHT processing.

UHT processing was performed using an Alfa Laval UHT (Type D) pilot scale plant (Alfa Laval, Lund, Sweden) operated in an indirect heating mode. The UHT section of the plant was a plate heat exchanger which used pressurized hot water as the heating medium. The UHT plant operating conditions are shown below:

Preheat temperature 75° C.
UHT temperature 140° C.
Feed flow rate 115–120 L h$^{-1}$

EXAMPLE 6

UHT Fouling Rates

Fouling Rate Determination

The rate of deposit formation on the heat exchanger surfaces (fouling rate) was determined by monitoring the rise in the temperature difference (ΔT) between the milk and the hot water (°C. h$^{-1}$). This was calculated by measuring the difference between the inlet hot water temperature and the outlet milk temperature from the UHT section. Measurements were made every 10 s by use of a datalogger. The fouling rate (°C. h$^{-1}$) for each UHT run was calculated from a linear regression of a plot of ΔT versus time.

Milk Composition

The detailed compositions of the β-LG AA and BB type milks used in these trials was determined as described by Hill (1993), Hill et al. (1993, 1995) and Hill and Paterson (1994).

The UHT fouling rates for the recombined variant milk powders are shown in FIGS. 1–4. In all cases the line across the figures at a fouling rate of 0.5° C./h corresponds to a UHT run time of approximately 8 hrs, which is the minimum run time which is normally required by UHT milk processors. The results from Trial 1 (FIG. 1) clearly show that β-LG AA type whole milk powder was not suitable for the UHT application, with the β-LG BB type whole milk powder giving significantly lower fouling rates than the whole milk powder made from the control milk (β-LG AB). Although the same trend was again observed in Trial 2 (FIG.

2), all three variant type powders generally gave lower UHT fouling rates than the corresponding mid season powders.

To further examine the findings from Trials 1 and 2, in Trial 3 (FIGS. 3 and 4) WMP manufactured from β-LG AA type milk fouled UHT plant rapidly and was not suitable for this application. Although not shown in FIG. 3 (because of the scale), the fouling rate of the low heat powder manufactured from β-LG AA type milk in a first run was 6.3° C./h and in a second run was 5.6° C./h. Apart from one run the β-LG BB type WMP of powder gave fouling rates below 0.5° C. and also significantly lower than those observed for the control milk. Generally the fouling rates were higher in the low heat WMPs than in the high heat WMPs for all three milk types. A medium preheat treatment β-LG AA type WMP gave the lowest fouling rate observed with this type of powder. No seasonal trend in the UHT fouling rate was apparent.

Figure 4:
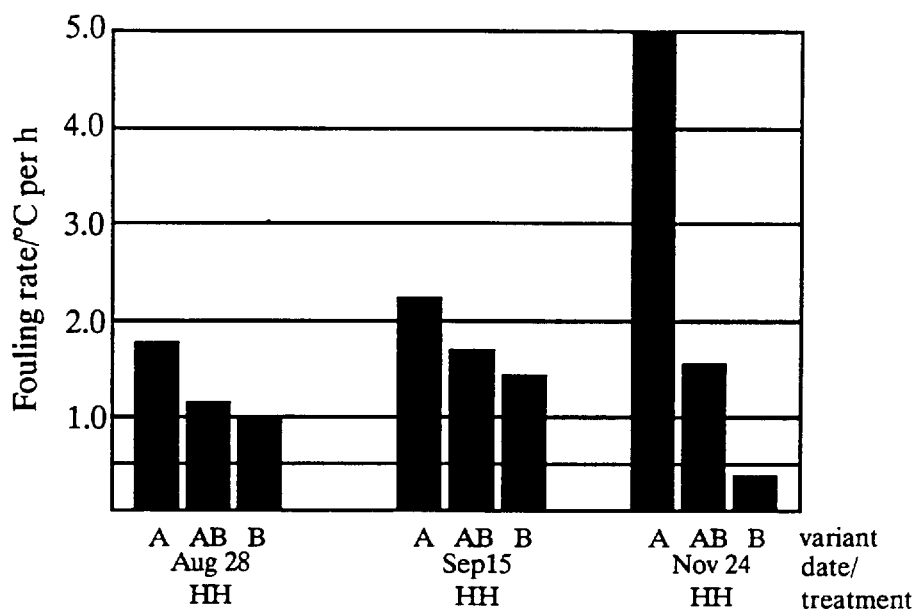
FIG. 4 is a bar graph similar to FIG. 3 in respect of Trial 3 but on skim milk powders.

FIG. 4 shows the UHT fouling rates of the variant SMPs manufactured during Trial 3. Although the trend AA>AB>BB was again observed, all powder types manufactured during the first and second runs had fouling rates above 0.5° C./h. Remarkably the β-LG AA type high heat SMP manufactured in a third run gave a UHT fouling rate of 13.7° C./h, compared with 1.5° C./h (β-LG AB) and 0.3° C./h (β-LG BB) type SMP fouling rates.

EXAMPLE 7

Figure 5:
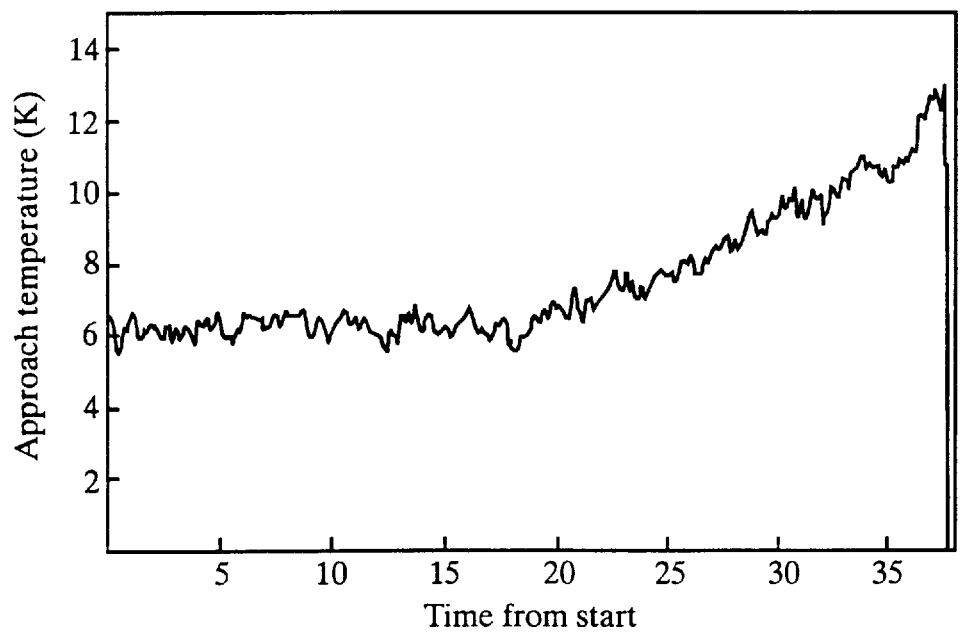
FIG. 5 is a plot of changes in approach temperature against the time in hours of milk powder manufacture.
Figure 6:
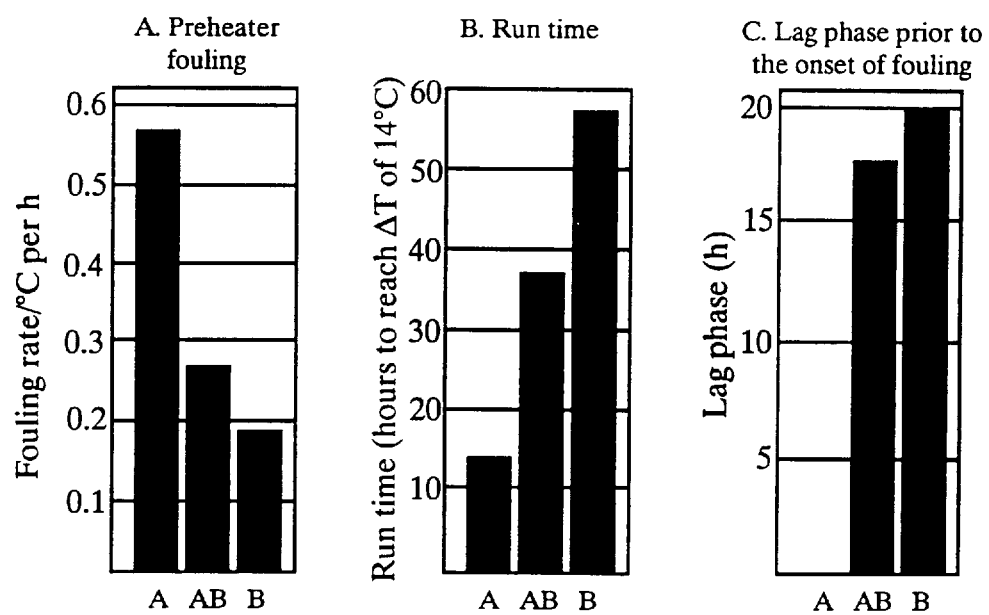
FIG. 6 is a series of bar graphs showing the effect of the β-lactoglobulin genetic variant on whole milk powder at manufacture.

Milk Powder Manufacture

β-LG variant had a marked effect on milk powder manufacture. With both β-LG BB type milk and the control milk (β-LG AB), a marked lag phase (FIG. 5) was observed before the onset of preheater fouling, but with β-LG AA type milk no lag was observed prior to preheater fouling. FIG. 6 shows the effect of β-LG variant on preheater fouling, the time taken to reach a temperature drop across the preheater of 14° C. and the length of the lag phase prior to the onset of preheater fouling. Clearly preheater fouling is higher with β-LG AA type milk (AA>AB>BB), the run time is shorter with β-LG AA type milk (AA<AB<BB) and time before the onset of fouling less with β-LG AA type milk (AA<AB<BB).

EXAMPLE 8

Milk Composition

The effect of β-LG variant on milk composition for Trials 1 and 2 is shown in Tables 3, 4, 5 and 6.

TABLE 3

The relationship between milk type and milk composition

| Comp % w/w | TRIAL 2 | | | TRIAL 1 | | |
|---|---|---|---|---|---|---|
| | AA | BB | AB | AA | BB | AB |
| Total protein | 3.36 | 3.38 | 3.49 | 3.13 | 3.16 | 3.27 |
| Casein | 2.48 | 2.61 | 2.75 | 2.49 | 2.66 | 2.54 |
| Whey protein | 0.88 | 0.77 | 0.74 | 0.64 | 0.50 | 0.73 |
| Fat | 4.92 | 5.41 | 5.05 | 4.12 | 4.62 | 4.58 |
| Lactose | 4.60 | 4.65 | 4.82 | 4.73 | 4.68 | 5.02 |
| Ash | 0.71 | 0.71 | 0.73 | 0.70 | 0.70 | 0.72 |
| Total solids | 13.54 | 14.10 | 13.93 | 12.46 | 13.23 | 13.59 |

TABLE 4

The relationship between milk type and mineral content

| Mineral mM/kg | TRIAL 2 | | | TRIAL 1 | | |
|---|---|---|---|---|---|---|
| | AA | BB | AB | AA | BB | AB |
| $Ca^{2+}$ | 31.87 | 32.26 | 33.40 | 31.33 | 31.08 | 31.80 |
| $PO_4^-$ | 21.04 | 21.80 | 21.60 | 22.53 | 23.05 | 23.80 |
| $Na^-$ | 17.85 | 17.59 | 17.28 | 15.70 | 15.83 | 14.90 |
| $K^-$ | 37.81 | 37.26 | 38.32 | 38.73 | 38.20 | 39.80 |
| $Cl^-$ | 30.35 | 29.35 | 30.24 | 30.73 | 30.76 | 31.60 |
| $Mg^{2-}$ | 4.74 | 4.64 | 4.64 | 4.13 | 4.13 | 4.10 |

TABLE 5

The relationship between milk type and the content of β-lactoglobulin and α-lactalbumin

| Protein | TRIAL 2 | | | TRIAL 1 | | |
|---|---|---|---|---|---|---|
| | AA | BB | AB | AA | BB | AB |
| β-LG g/L | 5.50 | 4.37 | 4.79 | 4.48 | 3.28 | 4.67 |
| α-LA g/L | 0.92 | 0.97 | 1.12 | 1.02 | 1.31 | 1.31 |

TABLE 6

The relationship between milk type and protein distribution

| Protein % | TRIAL 2 | | | TRIAL 1 | | |
|---|---|---|---|---|---|---|
| | AA | BB | AB | AA | BB | AB |
| Casein | 73.81 | 77.22 | 78.80 | 79.55 | 84.18 | 77.67 |
| Whey | 26.19 | 22.78 | 21.20 | 20.45 | 15.82 | 22.32 |

The relative differences in the compositions of the β-LG AA and BB type milks and control milk during different annual seasons (Hill et al., 1995) were very similar to those shown in Tables 2–5.

A detailed description of how the composition of milk produced under New Zealand farming conditions is affected by β-LG phenotype is discussed in detail in a number of papers (Hill, 1993, Hill et al., 1993, 1995, Hill and Paterson, 1994). The milk produced by β-LG BB phenotype cows contains more casein, fat and total solids than the milk produced by β-LG AA phenotype cows which contains more whey protein and β-LG. The content of milk minerals was very similar in both types of milk.

SUMMARY

All β-LG AA type milk powders fouled UHT plant at rates that would be considered commercially unacceptable, except those manufactured during late season. Even in Trial 2 the UHT fouling rates of recombined β-LG AA type powders were higher than either those given by the control powders or β-LG BB type powders (AA>AB>BB).

Figure 7:
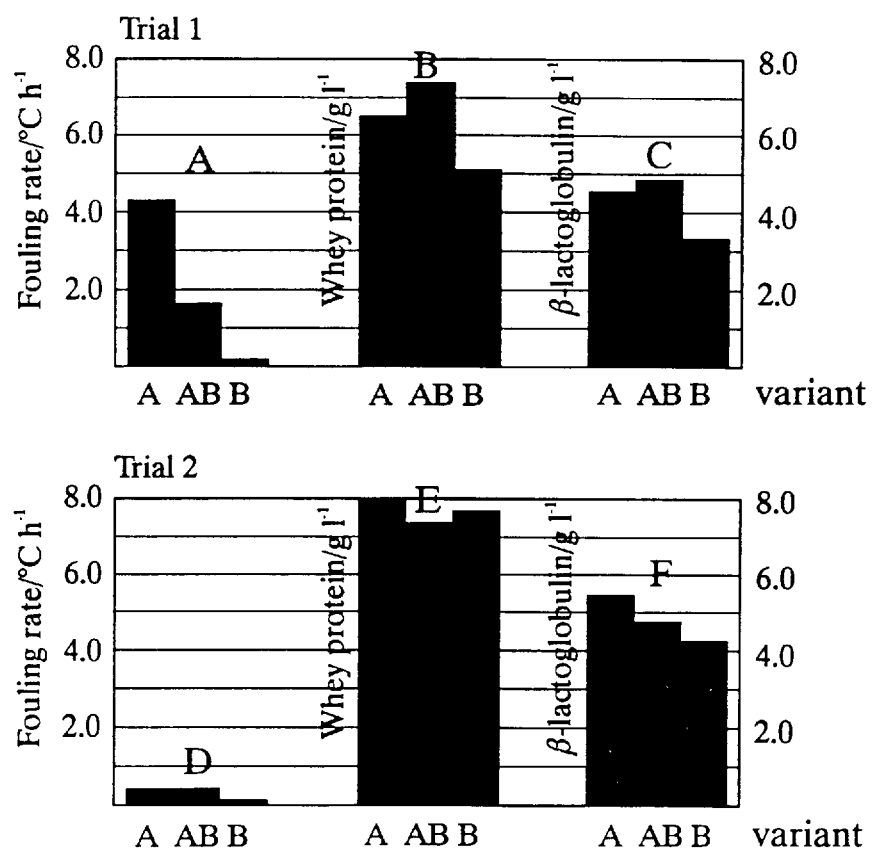
FIG. 7 is a series of bar graphs of the effect of β-lactoglobulin genetic variant on high heat powder (120° C./180s) UHT fouling rates, whey protein content and β-lactoglobulin content during Trials 1 and 2.

FIG. 7 shows the relationship between UHT fouling, whey protein concentration and β-LG concentration for the three high heat powder types in Trial 1 and Trial 2. There is no clear relationship between whey protein concentration or β-LG concentration and UHT fouling rate. In Trial 1 although the β-AA type milk contained more whey protein and β-LG than the β-LG BB type milk, it had a lower concentration of these milk components than the control (AB type) milk, yet still gave the highest fouling rate of the three milk powder types. In Trial 2, the concentrations of whey protein and β-LG were higher in all three milk types than the concentration of these milk components found in Trial 1, but the UHT fouling rates were lower than those observed in Trial 1. The β-LG concentration in the March β-LG BB type milk is almost the same as the β-LG concentration in the Trial 1 β-LG AA type milk.

In order to study the effect of β-LG variant on milk powder manufacturing properties the plate heat exchanger was used under conditions which were designed to give a high fouling rate. The flow rate used in the experiment (100 kg/h) was less than that which would generally be used in a commercial plant and thus fouling rates in the experiment are most likely to be higher than those which would be observed under truly commercial milk powder manufacturing conditions. However a commercial plant could not accept a three fold increase in approach temperature (5° to 15° C.) during a run. The experimental design did enable the marked differences in the behaviour of the variant milk types to be determined and showed that β-LG AA type milk is probably less suitable for the milk powder manufacturing process than β-LG BB type milk or the control (AB) milk.

EXAMPLE 8

Figure 8:
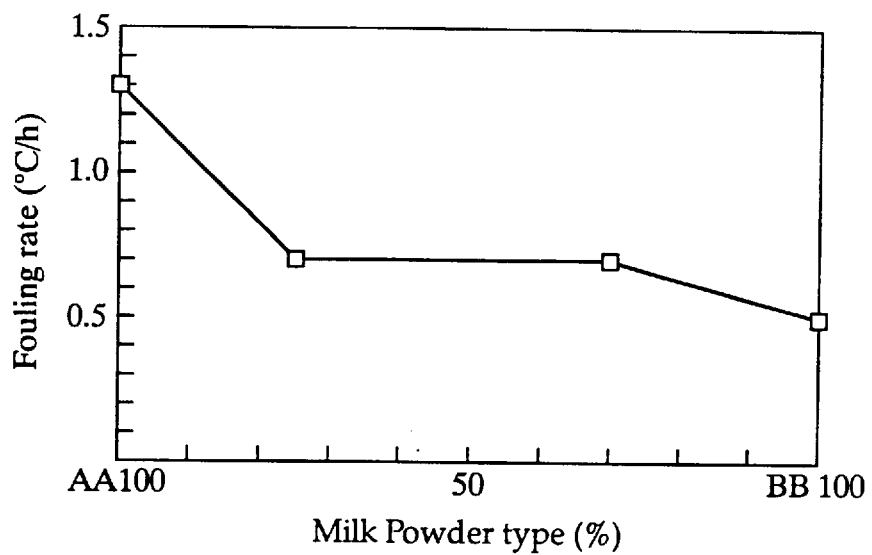
FIG. 8 is a plot of the UHT fouling rates of blended β-lactoglobulin AA and β-lactoglobulin BB whole milk sources.

Comparison of fouling rates between different blend ratios of high heat whole milk powders manufactured from β-lactoglobulin AA and BB phenotype cows High heat whole milk powders manufactured from the milk supplied by β-LG AA and BB phenotype cows were combined to produce large enough quantities of milk for UHT treatment The composite powders were blended at different ratios (see Table 7) to determine the effect of different levels of the powders manufactured from the milk supplied by β-LG AA and BB phenotype cows on the fouling rate of UHT plant. The fouling rates obtained from the blended powders are shown in FIG. 8.

TABLE 7

Blend ratios of β-lactoglobulin AA and BB composite powders

| Blend | Level of β-lactoglobulin AA (w % in blend) | Level of β-lactoglobulin BB (w % in blend) |
|---|---|---|
| 1 | 100 | 0 |
| 2 | 70 | 30 |
| 3 | 30 | 70 |
| 4 | 0 | 100 |

It will be seen from FIG. 8 that the highest fouling rate is achieved when the powder is made entirely from milk from β-LC AA phenotype cows. However, at blends containing even as little as 30 weight per cent of BB type there is a marked reduction in the fouling rate which may be acceptable for some applications.

REFERENCES

Hill, J. P. (1993). *The relationship between β-lactoglobulin phenotypes and milk composition in New Zealand dairy cattle*. Journal of Dairy Science, 76, 281–286.

Hill, J. P., Boland, M. J. & Creamer, L. K. (1993). *The alteration of bulk milk composition through the selection of β-lactoglobulin phenotypes*. Livestock Production Science, 35, 192–193.

Hill, J. P. & Paterson, G. R. (1994). *The variation of milk composition from individual β-lactoglobulin AA and BB phenotype cows*. Proceedings of the New Zealand Society of Animal Production 54, 293–295.

Hill, J. P., Paterson, G. R., Lowe, R. and Wakelin, M. (1995). *The effect of season and β-lactoglobulin phenotype on milk composition*. Proceedings of the New Zealand Society of Animal Production 55, 94–96.

Medrano, J. F. and Aguilar-Cordova, E. (1990). *Polymerase chain reaction amplification of bovine β-lactoglobulin genomic sequences and identification of genetic variants by RFLP analysis*. Animal Biotechnology, 1, 73–77.

Newstead, D. F. and Baucke, A. G. (1983). *Heat stability of recombined evaporated milk and reconstituted concentrated skim milk: Effects of temperature and time of preheating*. NZ Journal of Dairy Science and Technology, 18, 1–11.

New Zealand Dairy Board (1992) NZDB Laboratory Services Heat Stability Manual. New Zealand Dairy Board Laboratory, 114 Dominion Road, Auckland, New Zealand.

Ng-Kwai-Hang, K F and Grosclaude F (1992) *Advanced Dairy Chemistry—Vol* 1: *Proteins* (Ed. Fox P F) Elsevier Science Publishers Ltd, London, pp. 405–455.

Paterson, G. R., Hill, J. P. and Otter, D. E. (1995). *Separation of β-lactoglobulin A, B and C variants of bovine whey using capillary zone electrophoresis*. Journal of Chromatography A, 700, 105–110.

Singh, H. and Creamer, L. K. (1991). *Denaturation, aggregation and heat stability of milk protein during the manufacture of milk powder*. Journal of Dairy Research, 58, 269.

We claim:

1. A method of selecting milk for milk powder manufacturing properties which comprises testing milk from identified cows for the presence of variants of β-lactoglobulin and selecting those cows whose milk contains any non-fouling variant and does not contain any fouling variant, and milking separately the non-fouling variant milk producing cows and recovering and maintaining their milk separately from milk from any other source.

2. A method as claimed in claim 1 wherein said non-fouling variant is the B variant of β-lactoglobulin.

3. A method as claimed in claim 1 wherein said fouling variant is the A variant of β-lactoglobulin.

4. A method as claimed in claim 1 which includes the step of testing said resultant milk for the presence of any fouling variant and discarding any fouling variant found.

5. A method as claimed in claim 1 wherein said process includes the additional step of processing milk into a milk powder product.

6. A method as claimed in claim 5 wherein said additional step comprises UHT processing.

7. A milk powder product prepared by a process as claimed in claim 5.

8. A method as claimed in claim 1 wherein said method of testing is a phenotyping method.

9. A method as claimed in claim 8 wherein said phenotyping method comprises capillary electrophoresis.

10. A method as claimed in claim 8 wherein said phenotyping method comprises polyacrylamide gel electrophoresis.

11. Milk selected according to a method as claimed in claim 1.

12. A method according to claim 1 wherein the milk or milk product is goat's milk or milk product, sheep's milk or milk product, buffalo's milk or milk product, or milk or milk product from any other mammal which is fit for human consumption.

13. Milk or milk product prepared by the method according to claim 12.

14. A method as claimed in claim 1 which includes the additional step of blending up to 70% by weight of the combination of fouling milk with no less than about 30% by weight of the combination of said non-fouling milk.

15. A blended milk prepared by the method as claimed in claim 14.

16. A method for selecting breeding cows which produce daughters whose milk is non-fouling which comprises determining the genotype of said cows and selecting those whose daughters produce milk which does not contain the A-variant of β-lactoglobulin.

17. A method for selectively breeding bulls which produce daughters whose milk does not contain the A variant of β-lactoglobulin which comprises determining the genotype of said bulls and selecting those which daughters which produce milk which does not contain the A variant of β-lactoglobulin.

18. A method as claimed in claim 17 wherein said bulls are genotyped directly by using appropriate probes and polymerase chain reaction technology.

19. Bulls selected by the method as claimed in claim 17.

20. Semen of bulls as claimed in claim 19.

21. A method as claimed in claim 17 wherein said step of selecting daughters comprises phenotyping said daughters to determine the genotype of said bull by testing the milk of said daughters for absence of fouling variants of β-lactoglobulin and the presence of non-fouling variants of β-lactoglobulin.

22. A method as claimed in claim 16 wherein said cows are genotyped directly by using appropriate probes and polymerase chain reaction technology.

23. Cows selected by the method as claimed in claim 16.

* * * * *

UNITED STATES PATENT AND TRADEMARK OFFICE
CERTIFICATE OF CORRECTION

PATENT NO. : 5,850,804

DATED : December 22, 1998

INVENTOR(S) : Jeremy Paul Hill, Michael John Boland and Andrew Faulks Smith

It is certified that error appears in the above-identified patent and that said Letters Patent is hereby corrected as shown below:

On the cover page, at line [22], please replace "PCT Filed: May 22, 1996" with
--PCT Filed: May 20, 1996--

Signed and Sealed this

Thirty-first Day of August, 1999

*Attest:*

Q. TODD DICKINSON

*Attesting Officer*     Acting Commissioner of Patents and Trademarks